United States Patent [19]

Starchevich

[11] Patent Number: 5,429,615
[45] Date of Patent: Jul. 4, 1995

[54] INTRAVENOUS FLOW REGULATING AND MOUNTING ASSEMBLY

[76] Inventor: Jovanka Starchevich, 138 Sullivan St., New York, N.Y. 10012

[21] Appl. No.: 186,441

[22] Filed: Jan. 25, 1994

Related U.S. Application Data

[63] Continuation-in-part of Ser. No. 949,148, Sep. 22, 1992, Pat. No. 5,328,487.

[51] Int. Cl.⁶ .............................. A61M 5/00
[52] U.S. Cl. ........................ 604/246; 604/180; 251/7; 251/10; 248/74.2
[58] Field of Search ............... 604/246, 247, 118, 65, 604/67, 30, 32, 33, 36, 34, 80, 257, 131, 178, 253, 260, 180, 248, 249, 250, 25, 258; 128/DIG. 6, DIG. 12, DIG. 13; 251/6, 9, 10, 4; 248/74.1, 74.2, 75

[56] References Cited

U.S. PATENT DOCUMENTS

| | | | |
|---|---|---|---|
| 3,915,167 | 10/1975 | Waterman | 604/250 |
| 3,942,228 | 3/1976 | Buckman et al. | 251/4 |
| 4,061,142 | 12/1977 | Tuttle | 604/34 |
| 4,170,995 | 10/1979 | Levine et al. | 604/180 |
| 4,428,745 | 1/1984 | Williams | 604/6 |
| 4,434,963 | 3/1984 | Russell | 251/7 |
| 4,606,735 | 8/1986 | Wilder et al. | 604/180 |
| 5,005,793 | 4/1991 | Shillington . | |
| 5,014,962 | 5/1991 | Adelberg . | |
| 5,083,741 | 1/1992 | Sancoff | 251/9 |
| 5,203,056 | 4/1993 | Funk et al. | 24/543 |
| 5,203,769 | 4/1993 | Clement et al. | 604/32 |
| 5,209,441 | 5/1993 | Satoh | 248/74.2 |
| 5,238,218 | 8/1993 | Mackal | 251/10 |
| 5,259,587 | 11/1993 | D'Alessio et al. | 251/4 |
| 5,316,246 | 5/1994 | Scott et al. | 248/68.1 |

FOREIGN PATENT DOCUMENTS 0448202  3/1968  Switzerland ............... 248/74.1

Primary Examiner—C. Fred Rosenbaum
Assistant Examiner—V. Alexander
Attorney, Agent, or Firm—R. Neil Sudol; Henry D. Coleman

[57] ABSTRACT

An intravenous delivery assembly comprises, in accordance with the present invention, a frame member and a plurality of intravenous flow regulators each including (a) at least one attachment element for attaching a respective intravenous tube and (b) flow regulating componentry for varying a fluid flow rate through the respective intravenous tube. Cooperating connectors are provided on the flow regulators and the frame member for removably connecting the flow regulators to the frame member. The flow regulating componentry includes a clamping member having elongate first and second clamping elements and a slider member for shifting the clamping elements alternately towards and away from one another to vary a fluid flow cross-section in an intravenous tube inserted between the clamping elements.

20 Claims, 6 Drawing Sheets

INTRAVENOUS FLOW REGULATING AND MOUNTING ASSEMBLY

CROSS-REFERENCE TO A RELATED APPLICATION

This application is a continuation-in-part of U.S. patent application Ser. No. 07/949,148, filed Sept. 22, 1992, now U.S. Pat. No. 5,328,487.

BACKGROUND OF THE INVENTION

The invention relates to apparatus for mounting intravenous tubes and for controlling the flow of fluids through intravenous tubes. Intravenous tubes have been widely used for supplying nutrients and medication to patients. In many cases the same patient may have more than one such tube connected to his or her body. In some cases several tubes may be connected to each of several patients that are located in adjacent beds. In emergency situations it is of great importance to be able to quickly determine with absolute certainty which tube is connected to which patient and which nutrient or medication.

At least some of the prior art devices are extremely difficult to use. More specifically, at least one uses the combination of an inclined plane and a roller that is moved along the inclined plane to allow more or less flow through the intravenous tube. The so-called Adelberg clamp is delivered preassembled to the tube by the manufacturer or are delivered by the manufacturer as a set. Other devices are designed such that it is essential to have access to a free end of the intravenous tube because the clamp can only be slipped on the free end.

OBJECTS OF THE INVENTION

An object of the invention is to provide an intravenous flow regulating and mounting apparatus which facilitates organization of a large number of tubes, e.g., to prevent accidental shutoff, accidental release, or other changes resulting, for example, from pulling on an intravenous tube.

Another object of the invention to provide apparatus that will enable the health care professional to alternatively completely shut off flow or to modulate the flow to allow a selection of a desired flow rate.

It is still another object of the invention to provide apparatus which is inexpensive to manufacture.

It is also an object of the invention to provide apparatus that will work with any of various standard size intravenous tubing sizes.

Another object of the present invention is to provide an intravenous flow regulating and clamping assembly in which individual flow regulators can be selectively discarded.

These and other objects of the present invention will be apparent from the drawings and detailed descriptions herein.

SUMMARY OF THE INVENTION

An intravenous delivery assembly comprises, in accordance with the present invention, a frame member and a plurality of intravenous flow regulators each including (a) at least one attachment element for attaching a respective intravenous tube and (b) flow regulating componentry for varying a fluid flow rate through the respective intravenous tube. Cooperating connectors are provided on the flow regulators and the frame member for removably connecting the flow regulators to the frame member.

According to a preferred feature of the present invention, the flow regulating componentry includes a clamping member having elongate first and second clamping elements and a slider member for shifting the clamping elements alternately towards and away from one another to vary a fluid flow cross-section in an intravenous tube inserted between the clamping elements.

Where the clamping elements are legs of a U-shaped clamping component and the legs are interconnected by a bight portion of the U-shaped clamping component, the attachment element is a notch in the bight portion. An additional or alternative attachment element takes the form of a tooth on an edge of at least one of the legs projecting towards the other leg.

According to another feature of the present invention, each of the flow regulators includes a base, one of the legs being fixed to the base, another of the legs being movable relative to the base.

According to one embodiment of the present invention, the flow regulating componentry includes a roller mounted to a holder, the connectors being disposed on the holder.

According to a further feature of the present invention, the connectors may include dovetailing groove formations on the holder and the frame member for enabling a sliding interconnection of the flow regulators independently to the frame member. Alternatively, the connectors include a plurality of slidable locking elements on the frame member and keyways on the flow regulators.

A flow regulator for intravenous tubing comprises, in accordance with another conceptualization of the present invention, a clamping member having elongate first and second clamping elements in the form of legs of a U-shaped clamping component. The clamping elements or legs have inner faces facing one another and are interconnected by a bight portion of the U-shaped clamping component. The bight portion is provided with a notch for receiving an intravenous tube. In addition, the flow regulator includes means such as a slider member for shifting the legs alternately towards and away from one another to vary a fluid flow cross-section in the intravenous tube inserted between the legs.

A flow regulator for intravenous tubing comprises, in accordance with a further conceptualization of the present invention, a clamping member having elongate first and second clamping legs with inner faces facing one another. At least one of the legs is provided along an edge with a tooth projecting towards the other leg, for retaining the intravenous tube between the legs during an intravenous feeding operation. As before, a slider member is attached to the legs for shifting the legs alternately towards and away from one another to vary a fluid flow cross-section in an intravenous tube inserted between the legs.

A method for use in intravenous feeding comprises, in accordance with the present invention, the steps of (a) providing a plurality of intravenous tubes and a plurality of intravenous flow regulators each including flow regulating componentry for varying a fluid flow rate through a respective one of the intravenous tubes, (b) disposing a frame or holder member proximate to a patient, (c) attaching the intravenous tubes to the frame member via respective ones of the flow regulators upon disposition of the frame or holder member, and (d)

adjusting the flow regulating componentry of the respective flow regulators to provide for different flow rates through the intravenous tubes, depending on respective medical requirements.

According to another feature of the present invention, the intravenous tubes are preconnected to the flow regulators, and the attachment of the intravenous tubes to the frame member includes the step of attaching the flow regulators to the frame member.

Alternatively, the flow regulators are preconnected to the frame member, and the attachment of the intravenous tubes to the frame member includes the step of attaching the intravenous tubes to respective ones of the flow regulators.

In an intravenous flow regulating and clamping assembly in accordance with the present invention, individual flow regulators can be selectively discarded. The entire assembly need not be preassembled.

BRIEF DESCRIPTION OF THE DRAWING

The invention will be better understood by reference to the accompanying drawing in which.

DETAILED DESCRIPTION

Figure 1:
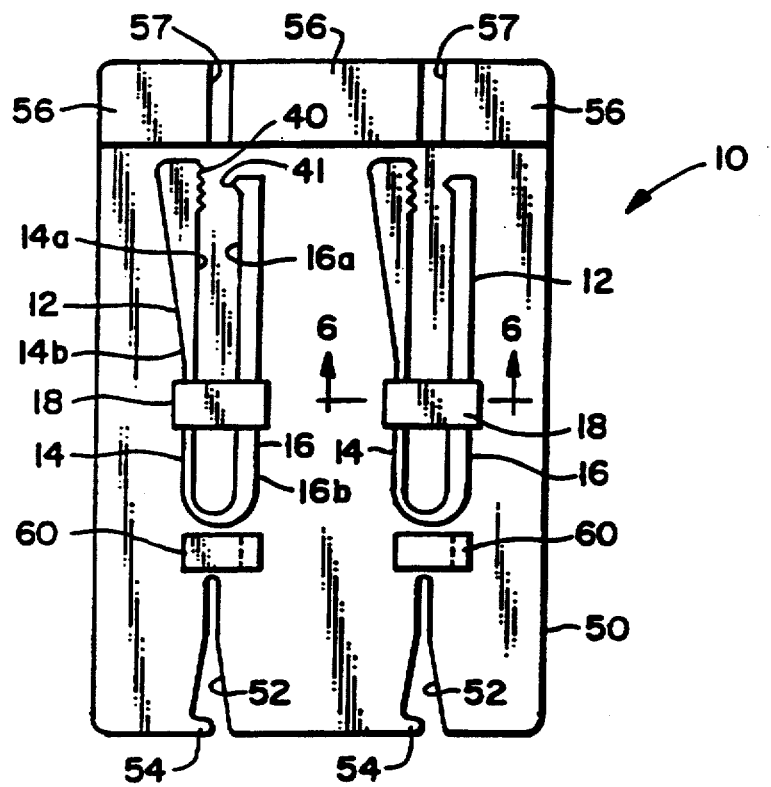
FIG. 1 is a plan view of an intravenous clamping and flow regulating device in accordance with one feature of the invention.
Figure 7:
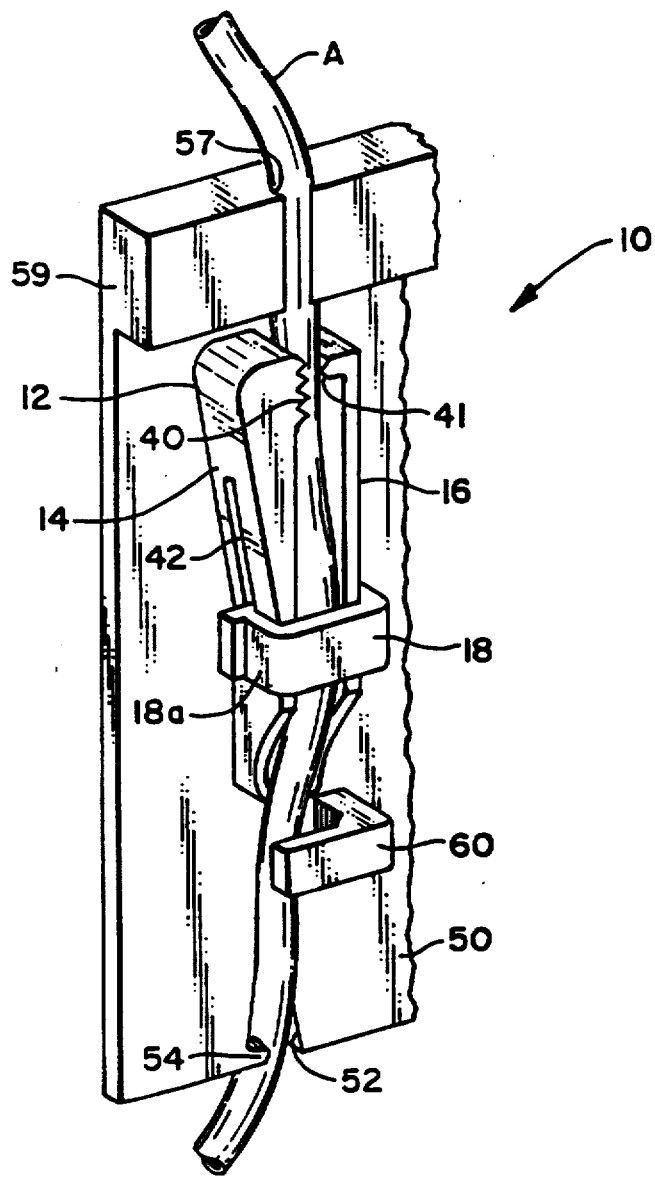
FIG. 7 is a fragmentary perspective view of a portion of the device of FIG. 1.

As illustrated in FIG. 1, a device 10 for engaging at least one associated intravenous tube A used in the delivery of medication or nutrient(s) to a patient includes a first generally U-shaped member 12 having first and second generally straight elongated legs 14, 16. Each of the legs 14, 16 have inner faces 14a and outer faces 14b. The inner faces 14a, 16a are disposed in opposed relation. The first leg 14 is movable between a first position in which the respective inner faces 14a, 16a of the first and second legs 14, 16 are disposed in spaced relation and a second position in which the respective inner faces 14a, 16a of the first and second legs 14, 16 are closer than in the first position. The inner faces 14a, 16a are disposed in the first position, illustrated in FIG. 1, with a space therebetween that is sufficient to allow insertion of an associated intravenous tube A. In the second position, illustrated in FIG. 7, the tube A is squeezed to shut off or modulate the flow through the intravenous tubing.

The device further includes a second generally U-shaped member 18 having first and second sides 18a, 18b engage the outer faces 14b, 16b of the first and second legs 14, 16 of the first generally U-shaped member 12. The second generally U-shaped member 18 may be slidable along a portion of the axial extent of the first and second legs 12, 14. As will be apparent from FIG. 6B the member 18 may be pivoted sufficiently to permit installation of the tube A by merely slipping an axial section under the member 18 and within the legs of the member 12. In other words it is not necessary to "thread" the end of the tube into device 10 as is the case with some prior art apparatus.

Figure 6A:
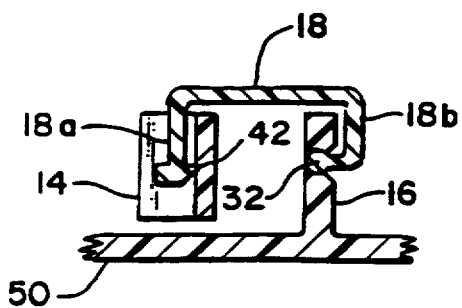
FIG. 6A is a fragmentary sectional view taken along the line 6—6 of FIG. 1.
Figure 6B:
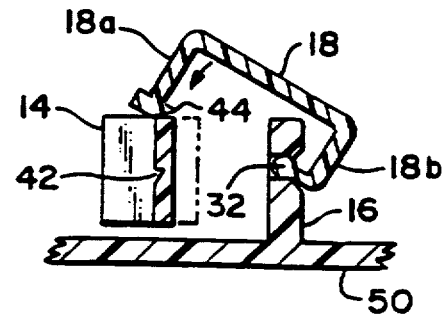
FIG. 6B is a view similar to the view of FIG. 6A showing an alternate position of the slider.
Figure 8:
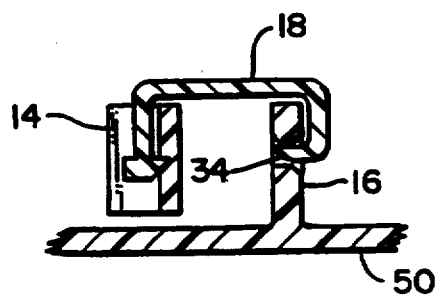
FIG. 8 is a view similar to that of FIG. 6A illustrating an alternative structure.
Figure 9:
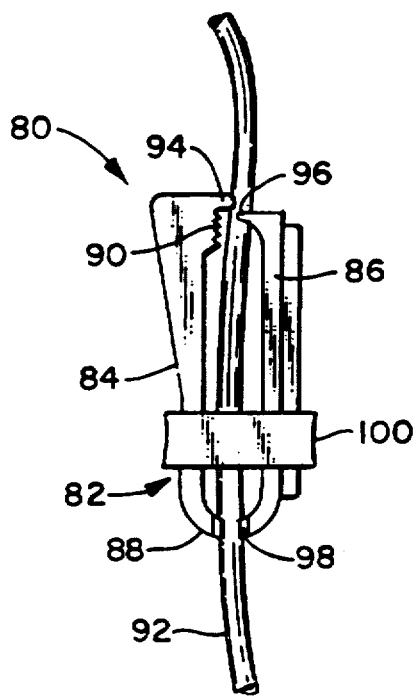
FIG. 9 is a schematic side elevational view of another intravenous clamping and flow regulating device in accordance with the present invention.

Preferably, the apparatus 20 includes means for engaging one of the legs of the first U-shaped member 12. The means for engaging, in the preferred embodiment, includes an enlongated slot 30 in the outer face 16b of the leg 16 of the first U-shaped member 12. In the preferred embodiement the means for engaging include an either cylindrical section shaped axial extremity 32 (as shown in FIGS. 6A and 6B) or a hook shaped axial extremity 34 (as shown in FIG. 8) which slide in and engage respectively with either a cylindrical shaped section shaped slot 30 or a rail shaped edge of the slot 30.

The first and second legs 14, 16 of the first generally U-shaped member 12 each have jaws on the inner faces 14a, 16a thereof that are disposed in opposed relationship and that are dimensioned and configured to squeeze the associated intravenous tube in the second position. More specifically, the first leg may be provided with a plurality of laterally extending teeth 40 on the inner face of 14a thereof. The inner face 16 has a single laterally extending ridge shaped surface 41 intended to concentrate forces against the intravenous tube A to either modulate or shut off fluid flow in the tube A. A groove 42 in the outer wall 14b is elongated and engages detent 44 on the outer face 14b of the leg 14.

In the preferred embodiment device 10 includes a generally planar base or carrier 50 that carries the first generally U-shaped member as best seen in FIGS. 1-3, 6A, and 6B. The base 50 includes a V-shaped slot 52 dimensioned and configured to permit insertion therein of the associated intravenuos tube A in a mammer to shut off fluid flow in the intravenous tube A.

Device 10 may further include means for partially blocking intravenous tube A access to the V-shaped slot 52. The means for blocking is disposed proximate to the open end of the V-shaped slot and is preferably a laterally extending member 54 that partially blocks access to the V-shaped slot 52. This ensures that the tube A does not accidentally fall into the V-shaped slot and thus inadvertently get shut off.

The geometric axis of the V-shaped slot 52 and the first generally U-shaped member are aligned and the apparatus may further include surface 56 for the placement of identifying indicia proximate to the first U-shaped member 12. The apparatus preferably includes a generally L-shaped member 60 extending from the base. The L-shaped member 60 is preferably dimensioned and configured to retain the associated intravenous tube A in the first U-shaped member and is disposed intermediate to the fisrt U-shaped member 12 and the V-shaped slot 52. A slot 57 is preferably disposed in a step shaped part 59 of the base 50 in aligned relation to the geometric axes of the V-shaped slot and the first U-shaped member 12. In various forms of the invention slot 57 may be cylindrical section shaped (not shown) or alternatively have opposed flat mutually parallel walls (not shown). The positive retention of the tube A in the slot 57 is important even if the member 12 is not engaging the tube A. More specifically, the positive location of the tube A is essential to the proper identification of respective tubes and thus the avoidance of errors as the result of confusing the tubes.

It will be seen that the slot 57 is a means for securing the associated intravenous tubing A to the base 50 and the slot 57 is disposed further from the V-shaped slot 52 that form the first U-shaped member 12.

In some forms of the invention, the base or carrier 50 is provided with a mounting surface 70 which in the preferred embodiment cooperates with a band (not shown) that typically will extend around the pole (not shown) which supports the intravenous fluid containers (not shown). Various other mounting means will be apparent to those skilled in the art.

It will be seen that the device in accordance with the invention allows the user to modulate the flow through the tube A by sliding the second U-shaped member along legs 14, 16 to cause the desired flow modulation or shutoff. The V-shaped slot is intended as a secondary shutoff means to absolutely insure no inadvertent fluid flow in the tube A.

A major advantage of the device in accordance with the invention is that the user may easily slip the tube A into the first U-shaped member 12. The ease of insertion will be apparent to those skilled in the field.

Figure 2:
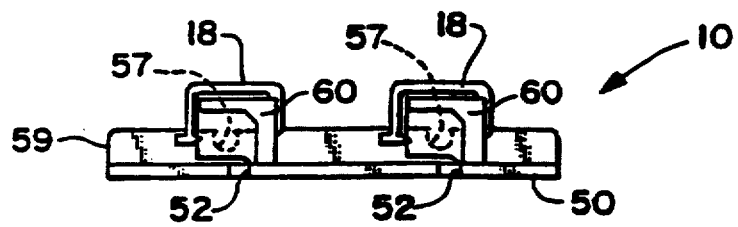
FIG. 2 is front elevational view of the device shown in FIG. 1.
Figure 3:
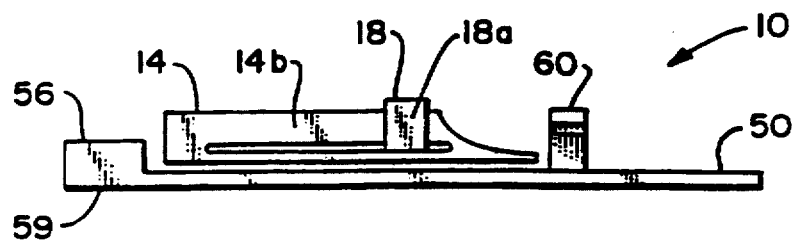
FIG. 3 is left elevational view of the device shown in FIG. 1.
Figure 4:
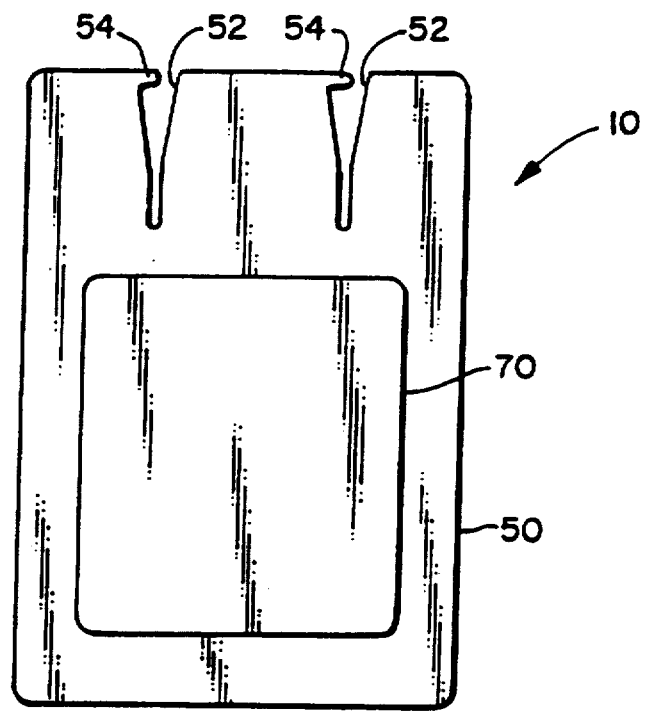
FIG. 4 is a bottom view of the device shown in FIG. 1.
Figure 5:
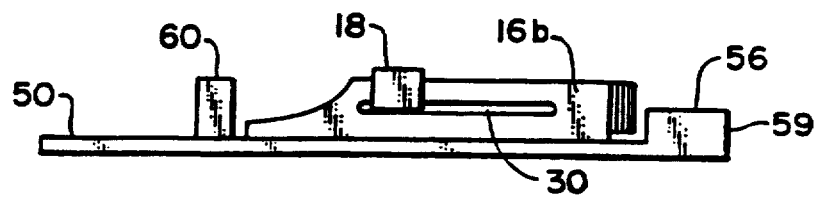
FIG. 5 is right elevational view of the device shown in FIG. 1.

For purposes of simplicity, FIGS. 1 and 2 show only two U-shaped clamping members 12. It will be apparent, however, that a larger number may be provided. Such an arrangement facilitates the orderly placement of the intravenous tubes with a minimum of risk or error and is particularly useful where a patient in surgery or intensive care must be supplied with a number of intravenous solutions. Pursuant to the embodiment of the invention illustrated in FIGS. 1 and 2, the clamping components are attached to base or carrier 50. Accordingly, in use, the entire assembly is disposed proximately to a patient, for example, on a wall or stand. Subsequently, intravenous tubes are inserted between legs 14 and 16 of respective clamping members 12. Slider members 18 are shifted respective distances along the U-shaped clamping members 12 to squeeze the intravenous tubes and restrict flow to a determinable degree.

In an alternative embodiment of the invention illustrated in FIGS. 9–12, an intravenous flow regulating or delivery assembly comprises a plurality of intravenous flow regulators 80 each including a generally U-shaped clamp 82 having two legs 84 and 86 connected to one another by a bight portion 88. At a free end, at least one leg 84 is provided with a plurality of serrations or teeth 90 for engaging an intravenous tube 92 and squeezing the tube to controllably restrict fluid flow therethrough. One or both legs 84 and 86 are additionally provided along one edge (see FIG. 11) with a respective retaining tooth 94 and 96 for enhancing the attachment of tube 92 to clamp 82, i.e., for retaining the tube between legs 84 and 86 during use of the device. Also for retention or attachment purposes, bight portion 88 is formed with a notch 98 which receives tube 92 without affecting the cross-sectional area of the tube lumen.

Figure 12:
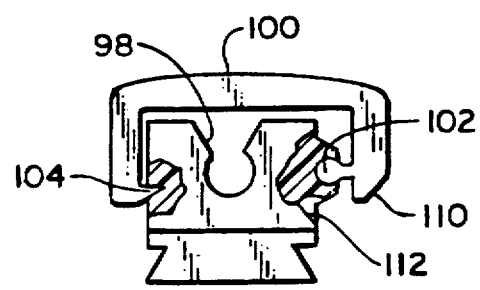
FIG. 12 is a schematic end elevational view, partially broken away, of the intravenous clamping and flow regulating device of FIGS. 9-11.

As shown in FIG. 12, a U-shaped slider member 100 is provided with a cylindrical lug 102 which is slidingly received in a cylindrical slot (not designated) in leg 86. On another side, slider member 100 is formed with an inwardly projecting detent 104 which is slidingly received in a snap-lock fit in a groove 106 (FIGS. 10 and 11) provided along an outwardly facing surface 108 of leg 84. In a region about lug 102, slider member 100 has a shoulder 110 which serves arrest function, limiting the angle taken by the slider member upon a rotation thereof about lug 102. Upon an outward rotation of slider member 100, preparatory to a removal or insertion of intravenous tube 92 between legs 84 and 86, shoulder 110 enters a recess 112 provided in leg 86.

Figure 10:
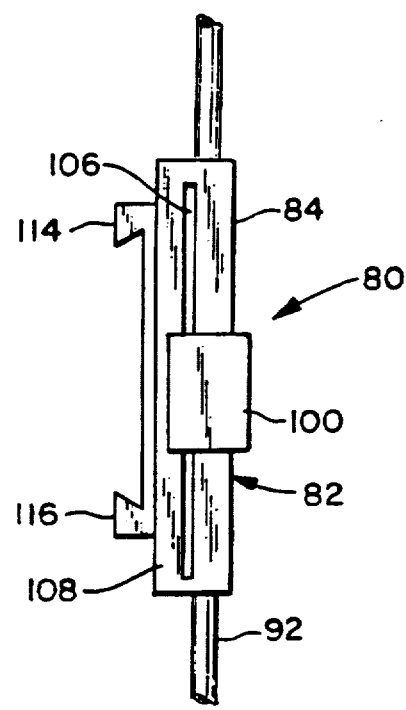
FIG. 10 is a schematic side elevational view, on a larger scale, of the intravenous clamping and flow regulating device of FIG. 9.
Figure 11:
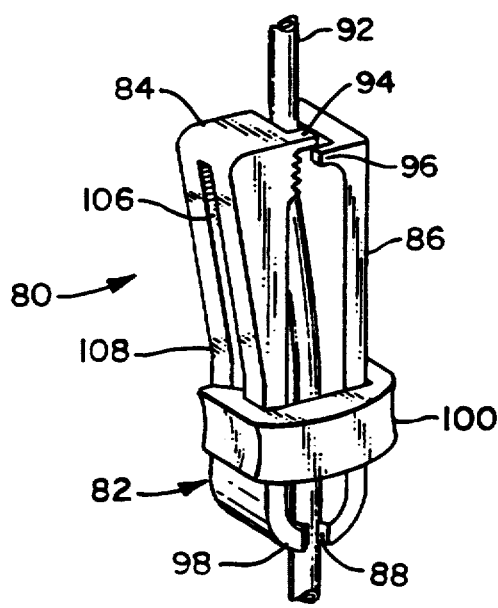
FIG. 11 is a schematic perspective view of the intravenous clamping and flow regulating device of FIGS. 9 and 10.
Figure 13:
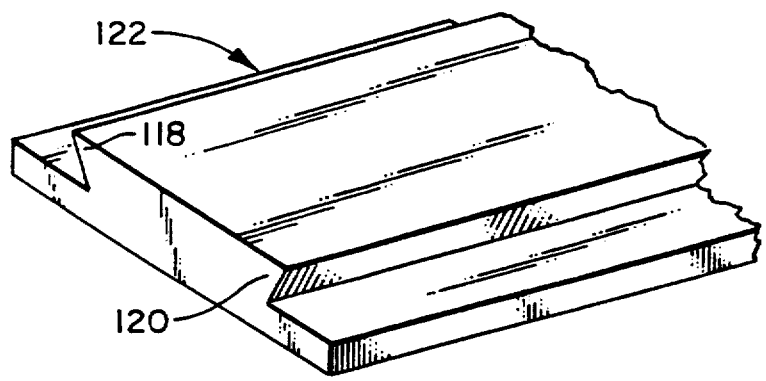
FIG. 13 is a partial perspective view of a frame member or holder for the clamping device of FIGS. 9-12.

As further illustrated particularly in FIG. 10, flow regulating device 80 is provided with a pair of dovetailed connectors 114 and 116 as a base affixed to leg 86 for cooperating with respective dovetailed edges 118 and 120 on a frame or bracket 122, shown in FIG. 13. Frame 122 is attached to a wall or to a stand, above a patient, and holds virtually any number of flow regulators 80.

Generally, it is contemplated that flow regulators 80 are slidingly attached to frame 122 upon a disposition thereof near a patient. Subsequently, respective intravenous tubes 92 are inserted between the legs 84 and 86 of clamps 82. It is also possible, however, for tubes 92 to be attached first to flow regulators 80, prior to the mounting thereof to frame 122.

Figure 14:
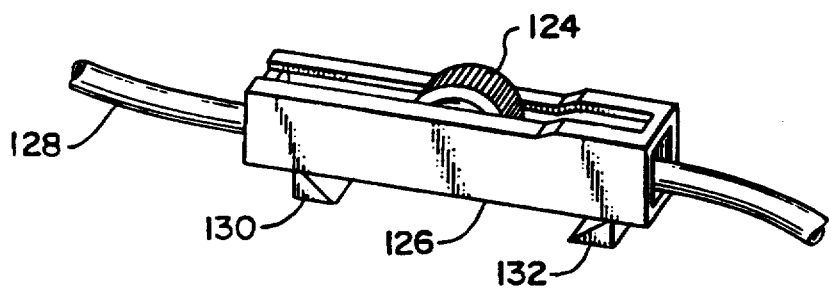
FIG. 14 is a perspective view of another intravenous flow regulating device removably attachable to the frame or holder of FIG. 13.

It is to be noted that other types of IV flow regulators may be attached to frame 122. FIG. 14 illustrates an IV flow regulator with a roller 124 mounted to a holder 126 or carrier. To varying degrees, depending on the desired flow rate, roller 124 presses an IV tube 128 which passes through holder 126. Dovetailed connectors 130 and 132 on holder 126 cooperate with respective dovetailed edges 118 and 120 on frame or bracket 122 to attach the regulator to the frame.

Figure 15:
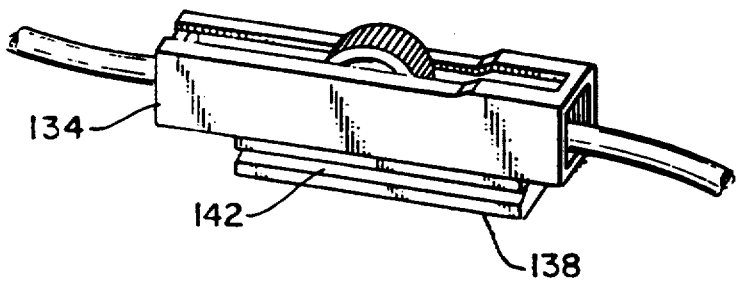
FIG. 15 is perspective view of another intravenous flow regulating device.
Figure 16:
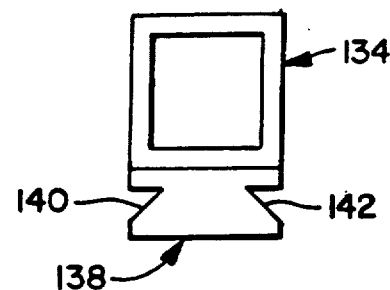
FIG. 16 is a schematic transverse cross-sectional view of the intravenous flow regulating device of FIG. 15.
Figure 17:
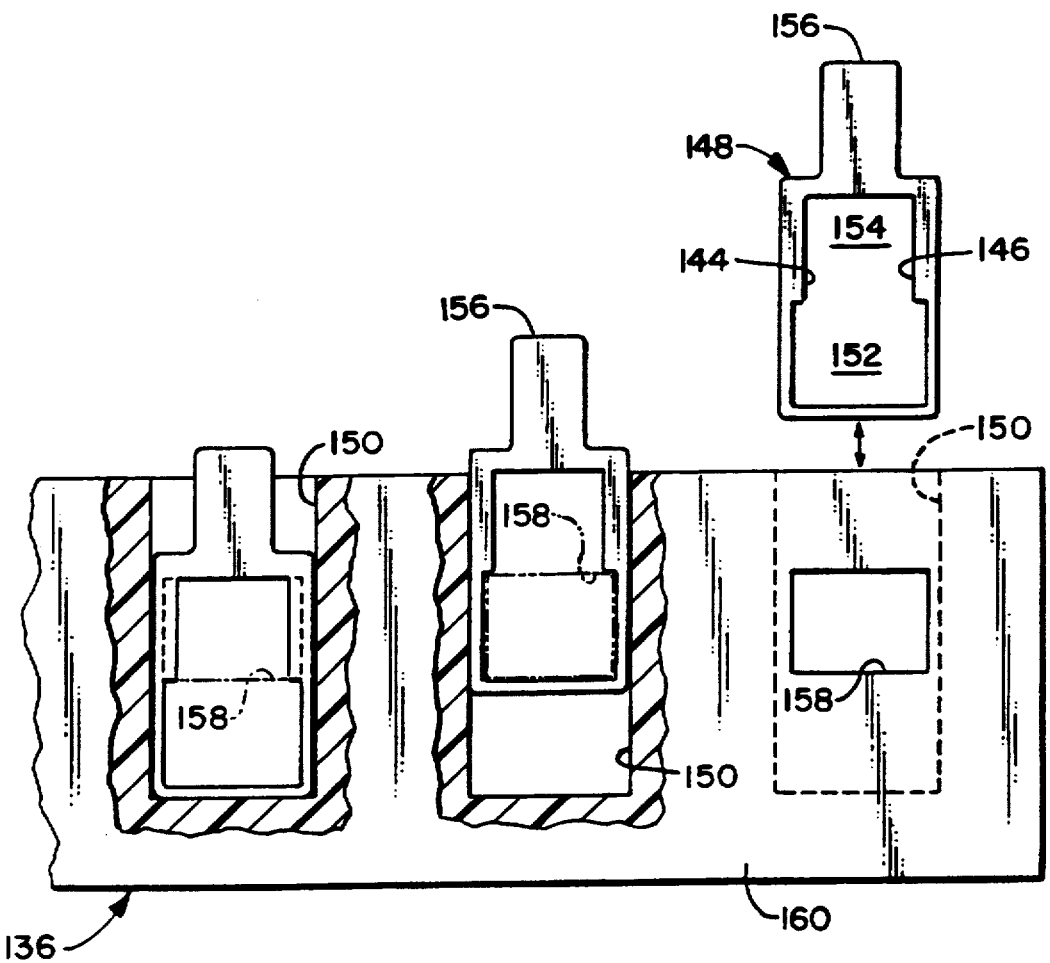
FIG. 17 is a schematic partial elevational view of a frame or bracket assembly for holding the device of FIG. 15.

As depicted in FIGS. 15–17, other structures are possible for releasably attaching an IV flow regulator/clamp 134 to a bracket 136. Regulator 134 is provided in a base or carrier part 138 with longitudinally extending grooves or keyways 140 and 142 (FIGS. 15 and 16). Grooves or keyways 140 and 142 slidingly receive inwardly facing edges 144 and 146 of a planar locking member 148 (FIG. 17). FIG. 17 shows a plurality of such locking members 148 inserted to different degrees in respective flat slots 150 in bracket 136. Each locking member 148 is provided with an opening having a large portion 152 and a smaller portion 154. Edges 144 and 146 define sides of smaller opening portion 154.

To attach flow regulator 134 to bracket 136, the user grasps a tab 156 on a selected locking member 148 and slides that locking member so that its large opening portion 152 is aligned with an aperture 158 in a front face or wall 160 of bracket 136. Base part 138 is then inserted through aperture 158 and large opening portion 152 to engage a rear wall 160 of bracket 136. Then locking member 148 is pushed into the respective slot 150 so that smaller opening portion 154 is aligned with aperture 158 and so that edges 144 and 146 are inserted into keyways 140 and 142, thereby locking the IV flow regulator 134 to bracket 136. Removal of the IV flow regulator from the bracket proceeds by reversing these steps.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An intravenous delivery assembly comprising:
   a plurality of modular intravenous flow regulators each including (a) a carrier, (b) attachment means connected to said carrier for attaching a respective intravenous tube and (c) flow regulating means mounted to said carrier for varying a fluid flow rate through the respective intravenous tube so that the flow rate assumes any of a plurality of different values between zero and a maximum flow rate;
   a frame member; and
   cooperating connector means on the carriers of said flow regulators and said frame member for removably connecting said flow regulators as modular units to said frame member.

2. The assembly defined in claim 1 wherein said flow regulating means includes:
   a clamping member having elongate first and second clamping elements, said clamping elements having inner faces facing one another; and
   means for shifting said clamping elements alternately towards and away from one another to vary a fluid flow cross-section in an intravenous tube inserted between said clamping elements, said means for shifting including a slider member attached to said clamping elements and slidable in a generally axial direction therealong.

3. The assembly defined in claim 2 wherein said clamping elements are legs of a U-shaped clamping component, said legs being interconnected by a bight portion of said U-shaped clamping component, said attachment means including a notch in said bight portion.

4. The assembly defined in claim 3 wherein one of said legs is fixed to the carrier of a respective flow regulator, another of said legs being movable relative to the carrier of the respective flow regulator.

5. The assembly defined in claim 3 wherein said attachment means includes a tooth on an edge of at least one of said legs projecting towards the other leg.

6. The assembly defined in claim 1 wherein said flow regulating means includes a roller mounted to the carrier of each respective intravenous flow regulator.

7. The assembly defined in claim 6 wherein said connector means includes means for enabling a sliding connection of the carriers of said flow regulators independently to said frame member.

8. The assembly defined in claim 7 wherein said connector means includes dovetailing groove formations on the carrier of each intravenous flow regulator and said frame member.

9. The assembly defined in claim 1 wherein said connector means includes a plurality of slidable locking elements on said frame member and keyways on said flow regulators.

10. A flow regulator for intravenous tubing, comprising:
    a clamping member having elongate first and second clamping elements, said clamping elements having inner faces facing one another, said clamping elements being legs of a U-shaped clamping component, said legs being interconnected by a bight portion of said U-shaped clamping component, said bight portion being provided with a notch for receiving an intravenous tube extending parallel to said clamping elements; and
    means different from the intravenous tube and connected to said legs for shifting said legs alternately towards and away from one another to vary a fluid flow cross-section in the intravenous tube inserted between said legs and into said notch, said means for shifting including a slider member attached to said legs and slidable in a generally axial direction therealong.

11. The flow regulator defined in claim 10 wherein at least one of said legs is provided with a tooth projecting towards the other leg, for retaining said intravenous tube between said legs during an intravenous feeding operation.

12. The flow regulator defined in claim 11 wherein said tooth extends from an edge of said one of said legs.

13. A flow regulator for intravenous tubing, comprising:
    a clamping member having elongate first and second clamping elements, said clamping elements having inner faces facing one another, said clamping elements being legs of a U-shaped clamping component, at least one of said legs being provided along an edge with a tooth projecting towards the other leg, for retaining said intravenous tube between said legs during an intravenous feeding operation; and
    means different from said intravenous tube and connected to said legs for shifting said legs alternately towards and away from one another to vary a fluid flow cross-section in an intravenous tube inserted between said legs, said means for shifting including a slider member attached to said legs and slidable in a generally axial direction therealong.

14. The flow regulator defined in claim 13 wherein said legs being interconnected by a bight portion of said U-shaped clamping component, said bight portion being provided with a notch for receiving said intravenous tube.

15. A method for use in intravenous feeding, comprising the steps of:
    providing a plurality of first intravenous tubes and a plurality of modular first intravenous flow regulators each including flow regulating means for varying a fluid flow rate through a respective one of said intravenous tubes;

disposing a frame member proximate to a patient;

upon disposition of said frame member, initially attaching said intravenous tubes to said frame member via respective ones of said flow regulators;

adjusting the flow regulating means of the respective flow regulators to provide for different flow rates through said intravenous tubes, depending on respective medical requirements;

subsequently attaching a modular second intravenous flow regulator to said frame member, said second intravenous flow regulator having flow regulating means for varying a fluid flow rate through a second intravenous tube; and upon completion of said step of subsequently attaching, adjusting the flow regulating means of said second intravenous flow regulator to provide for a respective flow rate through said second intravenous tube.

16. The method defined in claim 15 wherein said first intravenous tubes are preconnected to said first intravenous flow regulators, said step of initially attaching including the step of attaching said flow regulators to said frame member.

17. The method defined in claim 15 wherein said first intravenous flow regulators are preconnected to said frame member, said step of initially attaching including the step of attaching said first intravenous tubes to respective ones of said first intravenous flow regulators.

18. The method defined in claim 15 wherein each of said first intravenous flow regulators includes a clamping member having elongate first and second clamping elements, said clamping elements having inner faces facing one another and a shifting member slidably attached to said clamping elements, said step of adjusting the flow regulating means of said first intravenous flow regulators including the step of sliding said shifting member along said clamping elements.

19. A flow regulator for intrvenous tubing, comprising;

a clamping member having elongate first and second clamping elements, said clamping elements having inner faces facing one another, said clamping elements being legs of a U-shaped clamping component, said legs being interconnected by a bight portion of said U-shaped clamping component, said bight portion being provided with a notch for receiving an intravenous tube extending parallel to said clamping elements;

a base, one of said legs being fixed to said base, another of said legs being movable relative to said base; and means different from the intravenous tube and connected to said legs for shifting said legs alternately towards and away from one another to vary a fluid flow cross-section in the intravenous tube inserted between said legs and into said notch.

20. A flow regulator for intravenous tubing, comprising:

a clamping member having elongate first and second clamping elements, said clamping elements having inner faces facing one another, said clamping elements being legs of a U-shaped clamping component, at least one of said legs being provided along an edge with a tooth projecting towards the other leg, for retaining said intravenous tube between said legs during an intravenous feeding operation;

a base, one of said legs being fixed to said base, another of said legs being movable relative to said base; and means different from said intravenous tube and connected to said legs for shifting said legs alternately towards and away from one another to vary a fluid flow cross-section in an intravenous tube inserted between said legs.

* * * * *